(12) United States Patent
Curry

(10) Patent No.: US 6,699,909 B1
(45) Date of Patent: Mar. 2, 2004

(54) AMINOINDANES

(75) Inventor: Kenneth Curry, Vancouver (CA)

(73) Assignee: Prescient NeuroPharma Inc., Vancouver, B.C. (CA)

( * ) Notice: Subject to any disclaimer, the term of this patent is extended or adjusted under 35 U.S.C. 154(b) by 0 days.

(21) Appl. No.: 10/030,454

(22) PCT Filed: Jun. 30, 2000

(86) PCT No.: PCT/CA00/00757

§ 371 (c)(1),
(2), (4) Date: May 7, 2002

(87) PCT Pub. No.: WO01/02340

PCT Pub. Date: Jan. 11, 2001

(30) Foreign Application Priority Data

Jul. 2, 1999 (CA) .............................................. 2276931

(51) Int. Cl.⁷ ...................... A61K 31/195; C07C 229/02
(52) U.S. Cl. ........................ 514/567; 562/433; 562/458
(58) Field of Search ................................ 562/400, 405, 562/433, 458; 514/553, 561, 567

(56) References Cited

PUBLICATIONS

Journal of Organic Chemistry by Ma et al 64 pp 120–125 published on the Web Dec. 11, 1998.*
CA: 129:343698 abs of Peptides 1996 symposium Proceedings of European Peptide Symposium, 24th Edinburgh Sep. 8–13 pp 573–574 by Lehmann et al 1966.*
CA:95:610830 abs of Journal of Institution of Chemists (India) by GBautam et al 53(1) pp 27–29 1981.*
CA:136:310133 abs of Chinese Journal of Chemistry by Ding et al 19(12)pp 1232–8 2001.*
CA:130:177836 abs of Neuropharmacology by Thomsen et al 37(12) pp 1465–73 1998.*
CA:125:114326 abs of WO 9615099 May 1996.*
CA:135:267255 abs of WO2001072291 Oct. 2001.*
CA:135:132201 abs of Experimental Neurology by Faden et al 167(2) pp 435–44 2001.*

* cited by examiner

*Primary Examiner*—Jean F. Vollano
(74) *Attorney, Agent, or Firm*—Knobbe, Martens, Olson & Bear, LLP

(57) ABSTRACT

The present invention relates to therapeutically active novel aminoindanes of formula (I). Also provided is a method of preparing compounds of formula (I), and pharmaceutical compositions comprising the compounds. The novel compounds act as modulators of metabotropic glutamate receptors and, as such, are useful in treating diseases of the central nervous system related to the metabotropic glutamate receptor system.

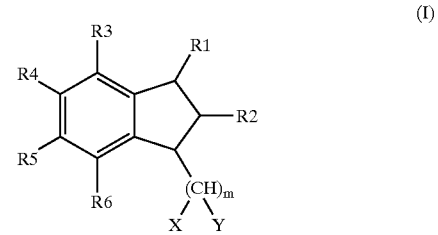

(I)

6 Claims, 1 Drawing Sheet

AMINOINDANES

CROSS REFERENCE TO RELATED APPLICATIONS

This application is the U.S. National Phase under 35 U.S.C. § 371 of International Application Number PC-T/CA00/00757, filed Jun. 30, 2000 and published in English, the United States designation of which claims priority under 35 U.S.C. § 119(a) to Canadian patent application number 2,276,931, filed Dec. Jul. 2, 1999. The Canadian application is herein incorporated by reference.

FIELD OF THE INVENTION

This invention pertains to therapeutically active novel aminoindanes, a method for preparing the same, pharmaceutical compositions comprising the compounds and a method of treating diseases of the Central Nervous System (CNS) therewith.

BACKGROUND OF THE INVENTION

The acidic amino acid L-glutamate is recognized as the major excitatory neurotransmitter in the CNS. The receptors that respond to L-glutamate are called excitatory amino acid receptors. The excitatory amino acid receptors are thus of great physiological importance, playing a role in a variety of physiological processes, such as long-term potentiation (learning and memory), the development of synaptic plasticity, motor control, respiratory and cardiovascular regulation, and sensory perception.

Excitatory amino acid receptors are classified into two general types and both are activated by L-glutamate and its analogs. Receptors activated by L-glutamate that are directly coupled to the opening of cation channels in the cell membrane of the neurons are termed "ionotropic." This type of receptor has been subdivided into at least three subtypes, which are defined by the depolarizing actions of the selective agonists N-Methyl-D-aspartate (NOVA), α-Amino-3-hydroxy-5-methylisoxazole-4-propionic acid (AMPA), and Kainic acid (KA).

The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function (Schoepp and Conn, *Trends in Pharmacological Science*, 14:13, 1993). Both types of receptors appear not only to mediate normal synaptic transmission along excitatory pathways but also to participate in the modification of synaptic connections during development and throughout life.

So far eight different clones of the G-protein-coupled mGluRs have been identified (Knopfel et al., 1995, *J. Med. Chem.*, 38, 1417–1426). These receptors function to modulate the presynaptic release of L-glutamate, and the postsynaptic sensitivity of the neuronal cell to L-glutamate excitation. Based on pharmacology, sequence homology and the signal transduction pathway that they activate, the mGluRs have been subclassified into three groups. The mGluR$_1$ and mGluR$_5$ receptors form group I. They are coupled to hydrolysis of phosphatidylinositol (PI) and are selectively activated by (RS)-3,5-dihydroxyphenylglycine (Brabet et al., *Neuropharmacology*, 34, 895–903, 1995). Group B comprises mGluR$_2$ and mGluR$_3$ receptors. They are negatively coupled to adenylate cyclase and are selectively activated by (2S,1'R,2'R,3'R)-2-(2,3-dicarboxycyclopropyl)glycine (DCG-IV; Hayashi et al., *Nature*, 366, 687–690, 1993). Finally, the mGluR$_4$, mGluR$_6$, mGluR$_7$ and mGluR$_8$ receptors belong to group III. They are also negatively coupled to adenylate cyclase and are selectively activated by (L)-2-amino-4-phosphonobutyric acid (L-AP4; Knopfel et al., 1995, *J. Med. Chem.*, 38, 1417–1426).

Agonists and antagonists of these receptors are believed useful for the treatment of acute and chronic neurodegenerative conditions, and as antipsychotic, anticonvulsant, analgesic, anxiolytic, antidepressant, and anti-emetic agents. Antagonists and agonists of neural receptors are classified as selective for a particular receptor or receptor subtype, or as non-selective. Antagonists may also be classified as competitive or non-competitive. While competitive and non-competitive antagonists act on the receptors in a different manner to produce similar results, selectivity is based upon the observations that some antagonists exhibit high levels of activity at a single receptor type, and little or no activity at other receptors. In the case of receptor-specific diseases and conditions, the selective agonists and antagonists are of the most value.

Compounds such as L-Glutamic acid, Quisqualic acid and Ibotenic acid are known to act as non-selective agonists on the mGluRs, while selective ionotropic glutamate receptor agonists such as NMDA, AMPA and kainate have little effect on these receptors. Recently a few compounds without activity at the ionotropic glutamate receptors but with activity at the metabotropic receptors have been identified. These include trans-ACPD (trans-(1S,3R)-1-aminocyclopentane-1,3-dicarboxylic acid), the partial agonist L-AP3 (L-2-amino-3-phosphonopropionic acid; Palmer, E., Monaghan, D. T. and Cotman, C. W. *Eur. J. Pharmacol.* 166, 585–587, 1989; Desai, M. A. and Conn, P. J. *Neuroscience Lett.* 109, 157–162, 1990; Schoepp, D. D. et al.,*J. Neurochemistry.* 56, 1789–1796, 1991; Schoepp D. D. and Johnson B. G. *J. Neurochemistry* 53, 1865–1913, 1989), L-AP4 (L-2-amino-4-phosphonobutyric acid) which is an agonist at the mGluR$_4$ receptor (Thomsen C. el al., *Eur. J. Pharmacol.* 227, 361–362, 1992) and some of the isomers of CCG (2-(carboxycyclopropyl)glycines) especially L-CCG-I and L-CCG-II (Hayashi, Y. et al., *Br. J. Pharmacol.* 107, 539–543, 1992).

Very few selective antagonists at the mGluRs have been reported. However some phenylglycine derivatives, S-4CPG (S-4-carboxyphenylglycine), S-4C3HPG (S-4-carboxy-3-hydroxyphenylglycine) and S-MCPG (S-α-methyl-4-carboxyphenylglycine) have been reported to antagonize trans-ACPD-stimulated phosphoinositide hydrolysis and thus possibly act as antagonists at mGluR$_1$ and mGluR$_5$ subtypes (Thomsen, C. and Suzdak, P, *Eur. J. Pharmacol.* 245, 299, 1993).

Research directed towards mGluRs is beginning to show that mGluRs may be implicated in a number of normal as well as pathological mechanisms in the brain and spinal cord. For example, activation of these receptors on neurons can: influence levels of alertness, attention and cognition; protect nerve cells from excitotoxic damage resulting from ischemia, hypoglycemia and anoxia; modulate the level of neuronal excitation; influence central mechanisms involved in controlling movement; reduce sensitivity to pain; reduce levels of anxiety.

The use of compounds active at the mGluRs for the treatment of epilepsy is corroborated by investigations of the influence of trans-ACPD on the formation of convulsions (Sacaan and Schoepp,*Neuroscience Lett.* 139, 77, 1992) and that phosphoinositide hydrolysis mediated via mGluR is increased after kindling experiments in rats (Akiyama et al. *Brain Res.* 569, 71, 1992). Trans-ACPD has been shown to increase release of dopamine in the rat brain, which indicates that compounds acting on the mGluRs might be usable for the treatment of Parkinson's disease and Huntington's Chorea (Sacaan et al., *J. Neurochemistry* 59, 245, 1992).

Trans-ACPD has also been shown to be a neuroprotective agent in a medial cerebral artery occlusion (MCAO) model in mice (Chiamulera et al. *Eur. J. Pharmacol.* 215, 353, 1992), and it has been shown to inhibit NMDA-induced neurotoxicity in nerve cell cultures (Koh v, *Proc. Natl. Acad. Sci. USA* 88, 9431, 1991). The mGluR-active compounds are also implicated in the treatment of pain. This is proved by the fact that antagonists at the mGluRs antagonize sensory synaptic response to nokious stimuli of thalamic neurons (Eaton, S. A. et al., *Eur. J. Neuroscience*, 5, 186, 1993).

The use of compounds active at the mGluRs for treatment of neurological diseases such as senile dementia have also been indicated by the findings of Zheng and Gallagher, *Neuron* 9, 163, 1992 and Bashir et al. (*Nature* 363, 347, 1993) who demonstrated that activation of mGluRs is necessary for the induction of long-term potentiation (LTP) in nerve cells (septal nucleus, hippocampus) and the finding that long-term depression is induced after activation of mGluRs in cerebellar granule cells (Linden et al. *Neuron* 7, 81, 1991).

Thus compounds that demonstrate either activating or inhibiting activity at mGluRs have therapeutic potential for the treatment of neurological disorders. These compounds have application as new drugs to treat both acute and chronic neurological disorders, such as stroke and head injuries; epilepsy; movement disorders associated with Parkinson's disease and Huntington's chorea; pain; anxiety; AIDS dementia; and Alzheimer's disease. Since the mGluRs can influence levels of alertness, attention and cognition; protect nerve cells from excitotoxic damage resulting from ischemia, hypoglycemia and anoxia; modulate the level of neuronal excitation; influence central mechanisms involved in controlling movement; reduce sensitivity to pain; and reduce levels of anxiety, these compounds can also be used to influence these situations and also find use in learning and memory deficiencies such as senile dementia. mGluRs may also be involved in addictive behaviour, alcoholism, drug addiction, sensitization and drug withdrawal (*Science*, 280:2045, 1998), so compounds acting at mGluRs might also be used to treat these disorders.

The current pharmaceutical options for treating neurological disorders tend to be very general and non-specific in their actions in that, although they may reduce the clinical symptoms associated with a specific neurological disorder, they may also negatively impact normal function of the central nervous system of patients. Thus new cellular targets and drugs that are more specific in their actions require to be identified and developed and thus a need remains for chemical compounds that demonstrate specific biding characteristics towards mGluRs.

Recently, Pelliari et al. (WO 96/15099) have disclosed certain amino carboxy compounds, including a specific class of 1-aminoindan dicarboxylic acid compounds and their use in treating diseases of central nervous system related to the metabotropic glutamate receptors systems.

SUMMARY OF THE INVENTION

Figure 1:
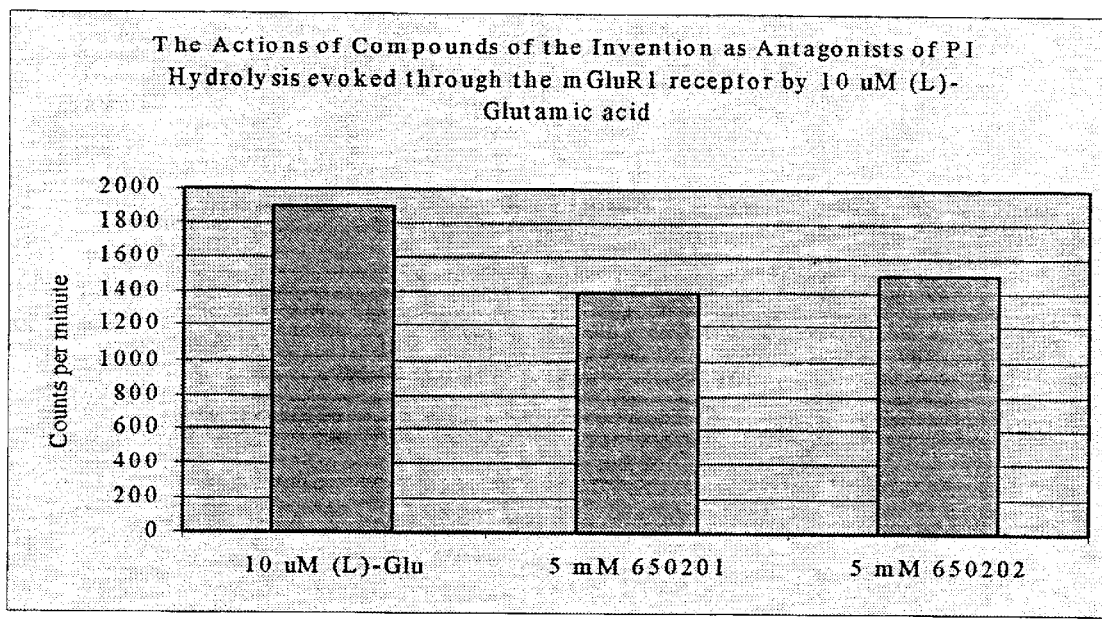
FIG. 1 demonstrates the actions of compounds of the present invention as antagonists of phosphatidyl inositol hydrolysis evoked through the mGluR1 receptor by 10 μM (L)-glutamine acid. (650201) corresponds to compound 4b and 650202 corresponds to compound 4a)

An object of the present invention is to provide novel aminoindanes that demonstrate activity at the various metabotropic glutamate receptors. In accordance with an aspect of the invention, there is provided a compound of formula (I):

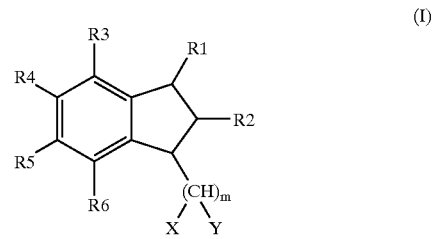

stereoisomers thereof, or pharmaceutically acceptable salts or hydrates thereof, wherein:

R1, and R2 are selected from the group comprising:
  1) H; or
  2) an acidic group selected from the group comprising carboxy, phosphono, phosphino, sulfono, X is an acidic group selected from the group comprising carboxy, phosphono, phosphino, sulfono, sulfino, borono, tetrazol, isoxazol;

Y is a basic group selected from the group comprising 1° amino, 2° amino, 3° amino, quaternary ammonium salts, aliphatic 1° amino, aliphatic 20 amino, aliphatic 3° amino, aliphatic quaternary ammonium salts, aromatic 1° amino, aromatic 2° amino, aromatic 3° amino, aromatic quaternary ammonium salts, imidazol, guanidino, boronoamino, allyl, urea, thiourea;

m is 0, 1; and

R3, R4, R5, R6 are independently H, nitro, amino, halogen, tritium, trifluoromethyl, trifluoroacetyl, sulfo, carboxy, carbamoyl, sulfamoyl or pharmaceutically acceptable esters or salts thereof.

DETAILED DESCRIPTION OF THE INVENTION

The terms and abbreviations used in the instant examples have their normal meanings unless otherwise designated. For example "° C." refers to degrees Celsius; "N" refers to normal or normality; "mmol" refers to millimole or millimoles; "g" refers to gram or grams; "ml" means milliliter or milliliters; "M" refers to molar or molarity; "p-" refers to para, "MS" refers to mass spectrometry; "IR" refers to infrared spectroscopy; and "NMR" refers to nuclear magnetic resonance spectroscopy.

As would be understood by the skilled artisan, throughout the synthesis of the compounds of Formula I it may be necessary to employ an amino-protecting group or a carboxy-protecting group in order to reversibly preserve a reactively susceptible amino or carboxy functionality while reacting other functional groups on the compound.

Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl)-isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxy-carbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decycloxy)benzyloxycarbonyl, isobornyloxycarbonyl, 1-piperidyloxycarbonlyl and the like; benzoylmethylsulfonyl group, 2-nitrophenylsulfenyl, diphenylphosphine oxide and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl (t-Boc), allyloxycarbonyl and benzyloxycarbonyl (CbZ). Further examples of these groups are found in E. Haslam, *Protecting Groups in Organic Chemistry*, (J. G. W. McOmie, ed., 1973), at Chapter 2; and T. W. Greene and P. G. M. Wuts, *Protective Groups in Organic Synthesis*, (1991), at Chapter 7.

Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, supra, at Chapter 5; and T. W. Greene and P. G. M. Wuts, supra, at Chapter 5.

The present invention provides a compound of the formula I:

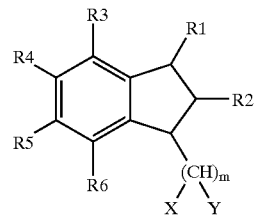

(I)

Stereoisomers thereof, or pharmaceutically acceptable salts or hydrates thereof, wherein:

R1, and R2 are selected from the group comprising
1) H
2) an acidic group selected from the group comprising carboxy, phosphono, phosphino, sulfono, sulfino, borono, tetrazol, isoxazol, —$(CH_2)_n$-carboxy, —$(CH_2)_n$-phosphono, —$(CH_2)_n$-phosphio, —$(CH_2)_n$-sulfono, —$(CH_2)_n$-sulfino, —$(CH_2)_n$-borono, —$(CH_2)_n$-tetrazol, and —$(CH_2)_n$-isoxazol, where n=1, 2, 3, 4, 5, or 6; or X is an acidic group selected from the group comprising carboxy, phosphono, phosphino, sulfono, sulfino, borono, tetrazol, isoxazol;

Y is be a basic group selected from the group comprising 1° amino, 2° amino, 3° amino, quaternary ammonium salts, aliphatic 1° amino, aliphatic 2° amino, aliphatic 3° amino, aliphatic quaternary ammonium salts, aromatic 1° amino, aromatic 2° amino, aromatic 3° amino, aromatic quaternary ammonium salts, imidazol, guanidino, boronoamino, allyl, urea, thiourea;

m can be 0, 1; and

R3, R4, R5, R6 are independently H, nitro, amino, halogen, tritium, trifluoromethyl, trifluoroacetyl, sulfo, carboxy, carbamoyl, sulfamoyl or pharmaceutically acceptable esters or salts thereof.

In one embodiment of the present invention a compound of formula (I) is provided, wherein: R1 is $CO_2H$, or $CH_2CO_2H$; R2 is H; X is $CO_2H$; and Y is $NH_2$ In another embodiment of the present invention a compound of formula (I) is provided, wherein: R1 is H; R2 is $CO_2H$ or $CH_2CO_2H$; X is $CO_2H$; and Y is $NH_2$.

Compounds of the present invention include, but are not limited to the following exemplary molecules:

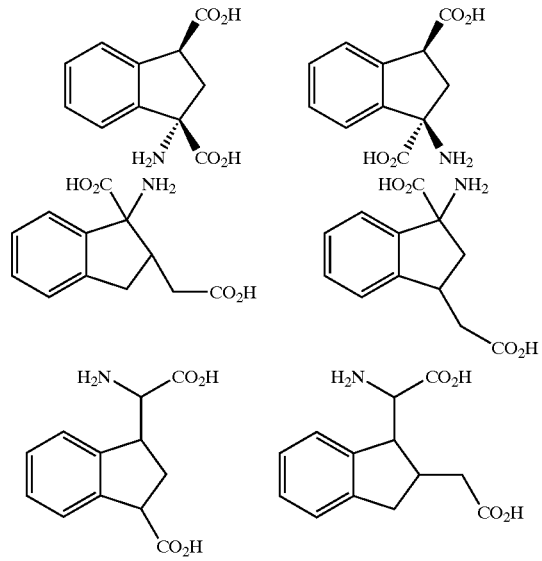

While all of the compounds of Formula I are believed to demonstrate activity at the metabotropic glutamate receptors (mGluRs), certain groups of Formula I compounds are more preferred for such use.

As noted supra, this invention includes the pharmaceutically acceptable salts of the compounds defined by Formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobroric acid, hydriodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like.

Preferred pharmaceutically acceptable acid addition salts are those formed with mineral acids such as hydrochloric acid and hydrobromic acid, and those formed with organic acids such as maleic acid and methanesulfonic acid.

Salts of amine groups may also comprise quarternary ammonium salts wherein the amino nitrogen carries a suitable organic group such as an alkyl, alkenyl, alkynyl, or aralkyl moiety.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, as long as the salt as a whole is pharmacologically acceptable and as long as the counterion does not contribute undesired qualities to the salt as a whole.

This invention further encompasses the pharmaceutically acceptable solvates of the compounds of Formula I. Many of the Formula I compounds can combine with solvents such as water, methanol, ethanol and acetonitrile to form pharmaceutically acceptable solvates such as the corresponding hydrate, methanolate, ethanolate and acetonitrilate.

The compounds of the present invention have multiple asymmetric (chiral) centers. As a consequence of these chiral centers, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

The prefixes "R" and "S" are used herein as commonly used in organic chemistry to denote the absolute configuration of a chiral center, according to the Cahn-Ingold-Prelog system. The stereochemical descriptor R (rectus) refers to that configuration of a chiral center with a clockwise relationship of groups tracing the path from highest to second-lowest priorities when viewed from the side opposite to that of the lowest priority group. The stereochemical descriptor S (sinister) refers to that configuration of a chiral center with a counterclockwise relationship of groups tracing the path from highest to second-lowest priority when viewed from the side opposite to the lowest priority group. The priority of groups is decided using sequence rules as described by Cahn et al., *Angew. Chem.*, 78, 413–447, 1966 and Prelog, V. and Helmchen, G.; *Angew. Chem. Int. Ed. Eng.*, 21, 567–583, 1982).

In addition to the R,S system used to designate the absolute configuration of a chiral center, the older D-L system is also used in this document to denote relative configuration, especially with reference to amino acids and amino acid derivatives. In this system a Fischer projection of the compound is oriented so that carbon-1 of the parent chain is at the top. The prefix "D" is used to represent the relative configuration of the isomer in which the functional (determining) group is on the right side of the carbon atom at the chiral center and "L", that of the isomer in which it is on the left.

As would be expected, the stereochemistry of the Formula I compounds is critical to their potency as agonists or antagonists. The relative stereochemistry is preferably established early during synthesis, which avoids stereoisomer separation problems later in the process. Subsequent synthetic steps then employ stereospecific procedures so as to maintain the preferred configuration. The preferred methods of this invention are the methods employing those preferred compounds.

Non-toxic metabolically labile esters and amides of compounds of Formula I are ester or amide derivatives of compounds of Formula I that are hydrolyzed in vivo to afford said compounds of Formula I and a pharmaceutically acceptable alcohol or amine. Examples of metabolically labile esters include esters formed with ($C_1$–$C_6$) alkanols in which the alkanol moiety may be optionally substituted by a ($C_1$–$C_8$) alkoxy group, for example methanol, ethanol, propanol and methoxyethanol. Examples of metabolically labile amides include amides formed with amines such as methylamine.

Preparation Of Compounds Of Formula (I)

According to another aspect, the present invention provides a process for the preparation of a compound of Formula I, or a pharmaceutically acceptable metabolically-labile ester or amide thereof, or a pharmaceutically acceptable salt thereof, which comprises:

(a) hydrolyzing a compound of formula (IIa) or (IIb):

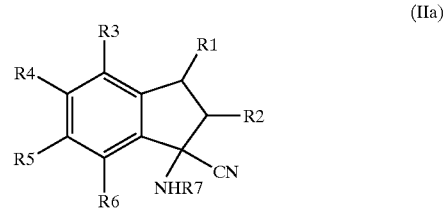

(IIa)

-continued

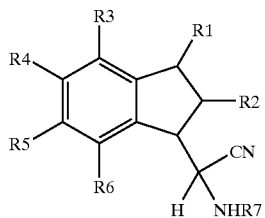
(IIb)

wherein:

R1, R2, R3, R4, R5 and R6 are as defined above. R7 is a hydrogen atom or an acyl group. Preferred functional groups for R7 are hydrogen and $(C_2-C_6)$ alkanoyl groups, such as acetyl; or (b) hydrolyzing a compound of formula (IIIa) or (IIb):

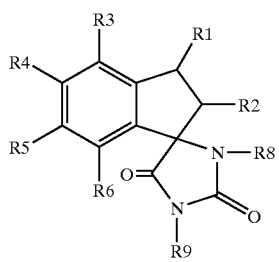
(IIIa)

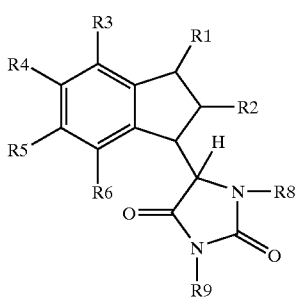
(IIIb)

wherein:

R1, R2, R3, R4, R5 and R6 are as defined above, R8 and R9 are each independently represent a hydrogen atom, a $(C_2-C_6)$ alkanoyl group, a $(C_1-C_4)$ alkyl group, a $(C_3-C_4)$ alkenyl group or a phenyl $(C_1-C_4)$ alkyl group, wherein the phenyl is unsubstituted or substituted by halogen, $(C_1-C_4)$ alkyl or $(C_1-C_4)$ alkoxy, or a salt thereof; or (c) deprotecting a compound of formula (IVa) or (IVb):

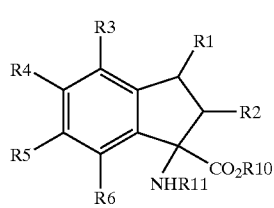
(IVa)

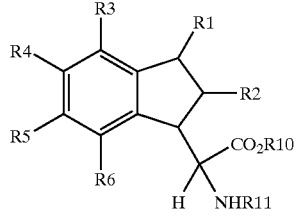
(IVb)

wherein:

R1, R2, R3, R4, R5 and R6 are as defined above and R10 is a hydrogen atom or a carboxyl protecting group, or a salt thereof, and R11 is a hydrogen atom or a nitrogen protecting group;

whereafter, if necessary and/or desired, the following steps are carried out:

(i) resolving the compound of Formula I;

(ii) converting the compound of Formula I into a non-toxic metabolically labile ester or amide thereof, and/or;

(iii) converting the compound of Formula I or a non-toxic metabolically labile ester or amide thereof into a pharmaceutically acceptable salt thereof.

Compounds of formulae (II), (III) and (IV), wherein at least one of R3, R4, R5 and R6 is other than H may be prepared from the compounds of formula (II), (III) and (IV) respectively, wherein: R3, R4, R5 and R6 is H, using standard reactions known to a person skilled in the art. For example: electrophilic substitution with appropriate electrophile, Friedel-Crafts alkylation or acylation, followed by further manipulations of the formed products within the knowledge of a worker skilled in the art.

The protection of carboxylic acid and amine groups is generally described in McOmie, *Protecting Groups in Organic Chemistry*, Plenum Press, NY, 1973, and Greene and Wuts, *Protective Groups in Organic Synthesis*, 2nd. Ed., John Wiley & Sons, NY, 1991. Examples of carboxy protecting groups include alkyl groups such as methyl, ethyl, t-butyl and t-amyl; aralkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl. Examples of amine protecting groups include acyl groups, such as groups of formula —C(O)R11 in which R11 represents $(C_1-C_6)$ alkyl, (3–10C) cycloalkyl, phenyl $(C_{1-6})$ alkyl, phenyl $(C_{1-6})$ alkoxy, or a $(C_3-C_{10})$ cycloalkoxy, wherein a phenyl group may optionally be substituted by one or two substituents independently selected from amino, hydroxy, nitro, halogeno, $(C_{1-6})$ alkyl, $(C_{1-6})$ alkoxy, carboxy, $(C_1-C_6)$ alkoxycarbonyl, carbamoyl, $(C_{1-6})$ alkanoylamino, $(C_{1-6})$ alkylsulphonylamino, phenylsulphonylamino, toluenesulphonylamino, and $(C_{1-6})$ fluoroalkyl.

The compounds of Formula II are conveniently hydrolyzed in the presence of an acid, such as hydrochloric acid or sulfuric acid, or a base, such as an alkali metal hydroxide, for example sodium hydroxide. The hydrolysis is conveniently performed in an aqueous solvent such as water and at a temperature in the range from 50° to 200° C.

The compounds of Formula III are conveniently hydrolyzed in the presence of a base, for example an alkali metal hydroxide such as lithium, sodium or potassium hydroxide, or an alkaline earth metal hydroxide such as barium hydroxide. Suitable reaction media include water. The temperature is conveniently in the range from 50° to 150° C.

The compounds of Formula IV may be deprotected by conventional methods. Thus, an alkyl carboxyl protecting group may be removed by hydrolysis. The hydrolysis may conveniently be performed by heating the compound of Formula IV in the presence of either a base, for example an alkali metal hydroxide such as lithium, sodium or potassium hydroxide, or an alkaline metal hydroxide, such as barium hydroxide, or an acid such as hydrochloric acid. The hydrolysis is conveniently performed at a temperature in the range from 10° to 300° C. An aralkyl carboxyl-protecting group may conveniently be removed by hydrogenolysis. The hydrogenolysis may conveniently be effected by reacting the compound of Formula IV with hydrogen in the presence of a Group VIII metal catalyst, for example a palladium catalyst such as palladium on charcoal. Suitable solvents for the reaction include alcohols such as ethanol. The reaction is conveniently performed at a temperature in the range from 0° to 100° C. An acyl amine protecting group is also conveniently removed by hydrolysis, for example as described for the removal of an alkyl carboxyl protecting group.

The compounds of Formula (IIa) and (IIb) may be prepared by reacting compounds of formula (Va) and (Vb) respectively:

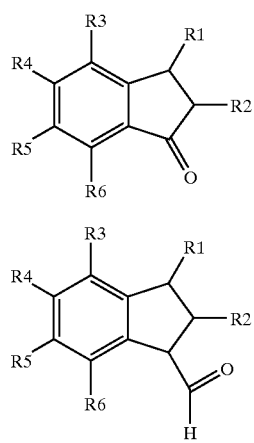

(Va)

(Vb)

wherein: R1, R2, R3, R4, R5 and R6 are as defined above; with an alkali metal cyanide, such as lithium, sodium or potassium cyanide, and either ammonium carbonate in an aqueous alcohol, such as aqueous ethanol, or with an ammonium halide, such as ammonium chloride, conveniently in the presence of ultrasound. If the reaction is conducted with ammonium carbonate, the reaction is conveniently performed at a temperature in the range from 35° C. to 150° C. If desired, the compounds of Formula II may then be alkylated, for example using a compound of formula RCl, wherein: R is ($C_{1-6}$) straight or branched chain alkyl, or ($C_{1-6}$) alkanoyl group. As described in more detail hereinafter, the alkylated compounds may be readily separated into their diastereomers. If the reaction is conducted with an ammonium halide in the presence of ultrasound, the ammonium halide is mixed with chromatography grade alumina in the presence of a suitable diluent such as acetonitrile. The mixture is then irradiated with ultrasound, whereafter the compound of Formula V is added, and the mixture is again irradiated. The alkali metal cyanide is then added, followed by further irradiation with ultrasound.

Individual isomers of compounds of Formula (IIa) and (IIb) may be made by reacting a compound of the Formula V with the stereoisomers of the chiral agent (S)- and (R)-phenylglycinol and a reactive cyanide such as trimethylsilyl cyanide to form the intermediate compounds of Formula (VIa) or (VIb), that can be further hydrolysed to give the desired products.

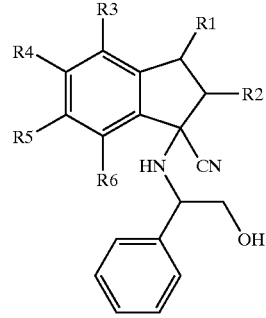

(VIa)

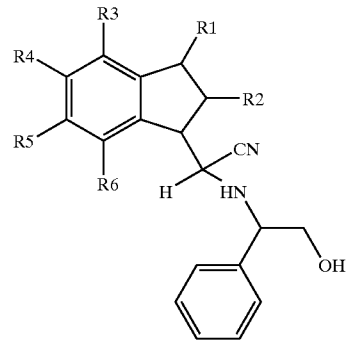

(VIb)

The compounds of Formula III may be prepared by reacting a compound of Formula V with an alkali metal cyanide, such as lithium, sodium or potassium cyanide, and ammonium carbonate or ammonium carbamate. Common solvents include alcohols, such as methanol, aqueous methanol and aqueous ethanol. Conveniently the reaction is performed at a temperature in the range of from 10° to 150° C. If desired, the compounds of Formula III may then be alkylated, for example using an appropriate alkyl, aryl or acyl chloride.

The compounds of Formula (Va) are either commercially available or may be prepared using standard procedures known to a person skilled in the relevant art. For example: compounds of formula (Va) can be prepared by reacting a compound of Formula VII with thionyl chloride or phosphorus pentachloride, and subjecting the resulting compound to the Friedel-Crafts acylation conditions.

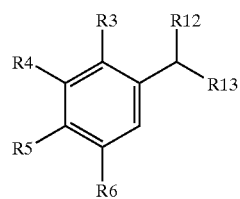

VII wherein: R12 and R13 are together or independently $CO_2H$ or $CH_2CO_2H$

In an alternative manner the compounds of formula (Va) can be prepared from compound VIII, by alkylation, followed by hydrolysis of the resulting compounds.

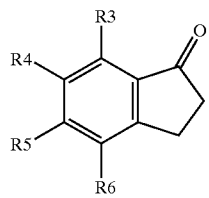

VIII

Compounds of formulae (VII), and (VII) are either commercially available or may be prepared using standard procedures known to a person skilled in the art. Compounds of formulae (VII), and (VII) wherein at least one of R3, R4, R5 and R6 is other than H may be prepared from the compounds of formulae (VII), and (VII) respectively, wherein R3, R4, R5 and R6 is H, via standard reactions known to a person skilled in the art. For example: electrophilic substitution with appropriate electrophile, Friedel-Crafts alkylation or acylation, followed by further manipulations of the formed products within the knowledge of a worker skilled in the art.

The compounds of formula (Vb) may be prepared by reacting a compound of formula (Va) with Wittig salt such as (alkoxy methyl)triphenylphosphonium halide in the presence of alkali metal salt of bis (trimethylsilyl) amine or by reacting a compound of formula (Va) with Wittig reagent such as $Ph_3P=CHOCH_3$, followed by reaction with trimethylsilyl halide.

Compounds of formulae (Va), and (Vb), wherein at least one of R3, R4, R5 and R6 is other than H may be prepared from the compounds of formula (Va) and (Vb) respectively, wherein R3, R4, R5 and R6 is H, using standard reactions known to a person skilled in the art. For example: electrophilic substitution with appropriate electrophile, Friedel-Crafts alkylation or acylation, followed by further manipulations of the formed products within the knowledge of a worker skilled in the art.

In an alternative manner, compounds of formula (V) may be prepared as taught in U.S. Pat. Nos: 5,329,049; and 5,360,936.

Many of the intermediates described herein, for example the compounds of Formula II, III and IV are believed to be novel, and are provided as further aspects of the invention.

Biological and Therapeutic Activity Of Compounds Of Formula (I)

The compounds of formula I of the present invention exhibit agonists or antagonists activity toward certain metabotropic glutamate receptors (mGluRs). Therefore, another aspect of the present invention provides a method of modulating the activity of mGluRs in mammals, which comprises administering to a mammal requiring modulated excitatory amino acid neurotransmission a pharmacologically-effective amount of a compound of Formula I. The term "pharmacologically-effective amount" is used to represent an amount of the compound of the present invention that is capable of affecting the mGluRs. By modulating mGluR activity, a compound of the present invention is acting as an agonist or antagonist of mGluR. When a compound of the present invention acts as an agonist, the interaction of the compound with the excitatory amino acid receptor mimics the response of the interaction of this receptor with its natural ligand, (i.e. L-Glutamic acid). When a compound of the invention acts as an antagonist, the interaction of the compound with the excitatory amino acid receptor blocks or attenuates the response of the interaction of this receptor with its natural ligand, (i.e. L-Glutamic acid).

The particular dose of compound administered according to the present invention will, of course, be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.001 mg/kg to about 100 mg/kg of the active compound of this invention. Preferably, daily doses will be about 0.05 mg/kg to about 50 mg/kg, more preferably from about 0.1 mg/kg to about 20 mg/kg.

A variety of physiological functions have been shown to be subject to influence by excessive or inappropriate stimulation of excitatory amino acid transmission. The Formula I compounds of the present invention are believed (through their interactions at the mGluRs) to have the ability to treat a variety of neurological disorders in a warm-blooded mammals associated with abnormal excitatory amino acid transmission, including but not limited to acute neurological disorders such as cerebral deficits subsequent to cardiac bypass surgery and grafting, cerebral ischemia (e.g. stroke and cardiac arrest), spinal cord trauma, head trauma, perinatal hypoxia, and hypoglycemic neuronal damage. Similarly, the Formula I compounds of the present invention, through their modulation of mGluR activity are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idiopathic and drug-induced Parkinson's disease. The present invention also provides methods for treating these disorders which comprises administering to a patient in need thereof an effective amount of a compound of Formula I.

The Formula I compounds of the present invention, through their modulation of mGluR activity are also believed to have the ability to treat a variety of other neurological disorders in mammals that are associated with glutamate dysfunction, including muscular spasms, convulsions, migraine headaches, urinary incontinence, psychosis, drug tolerance, withdrawal, and cessation (i.e. opiates, benzodiazepines, nicotine, cocaine, or ethanol), smoking cessation, anxiety and related disorders (e.g. panic attack), emesis, brain edema, chronic pain, sleep disorders, Tourette's syndrome, attention deficit disorder, and tardive dyskinesia. Therefore, the present invention also provides methods for treating these disorders which comprise administering to a patient in need thereof an effective amount of the compound of Formula I.

The Formula I compounds of the present invention, through their modulation of mGluR activity are also believed to have the ability to treat a variety of psychiatric disorders, such as schizophrenia, anxiety and related disorders (e.g. panic attack), depression, bipolar disorders, psychosis, and obsessive compulsive disorders. The present invention also provides methods for treating these disorders which comprises administering to a patient in need thereof an effective amount of a compound of Formula I.

Functional Assays Employing Cloned Subtypes of Metabotropic Receptors

The pharmacological properties of the compounds of the present invention can be determined via appropriate functional assays using recombinant metabotropic glutamate receptors. For example adenylate cyclase assays or phosphatidylinositol hydrolysis assays, performed using standard procedures, can be used to determine agonist or antagonist activity towards mGluRs.

In Vitro Testing:

General in vitro assay methods include monitoring of adenylate cyclase activity and phosphatidyl inositol hydrolysis in a cell line that expresses the appropriate mGluR.

(a) Adenylate Cyclase Activity

Adenylate cyclase activity is determined in initial experiments in transfected mammalian cells, using standard techniques. See, e.g., N. Adhar, et al., Supra; R. L. Weinshank, et al. Proc. Natl. Acad. Sci. (USA), 89:3630–3634 (1992), and the references cited therein.

Mammalian cells (the cell line AV12-664 is especially preferred) are stably transfected with a plasmid comprising the cloned metabotropic glutmate receptor. The cells are maintained in aa appropriate medium, for example one consisting of Dulbecco's Modified Eagle's Medium (DMEM) containing 5% dialyzed fetal calf serum, 10 mM HEPES buffer (pH 7.3), 1 mM sodium pyruvate, 1 mM glutamine, and 200 $\mu$.g/mL hygromycin.

For the assay the cells are disassociated from stock culture flasks with trypsin, and plated in 24-well plastic tissue culture dishes (15 mm wells) at a density of 500,000–700,000 cells per well using the same culture medium. After a twenty four hour incubation in a humidified $CO_2$ incubator, the cell monolayers are washed with buffer (for example Dulbecco's phosphate-buffered saline containing 0.5 mM IBMX and 3 mM glucose) and then incubated in the same buffer at 37° C. for 30 minutes. The monolayers are then washed with six exchanges of buffer.

Test compound(s) and forskolin, or forskolin alone, dissolved in buffer, are added after the final wash. After incubating for 20 minutes at 37° C., 0.5 mL of 8 mM EDTA is added to each well. The plates are then placed in a boiling water bath for about four minutes. The supernatant fluids are recovered from the wells and lyophilized. Cyclic AMP (cAMP) determinations are carried out on the lyophilized samples using commercially available radioimmunoassay kits, following the manufacturer's instructions. The cAMP levels in wells containing test compound(s) are then compared to the forskolin controls.

(b) Phosphatidylinositol Assay

Phosphatidylinositol hydrolysis is measured in clonal cell lines (for example AV12) harbouring a plasmid expressing the cloned metabotropic glutamate receptor in response to addition of glutamate agonists, as a functional assay for metabotropic glutamate receptor activity according to D. Schoepp, Trends in Pharmaceutical Sciences, 11:508, 1990.

Twenty four well tissue culture vessels are seeded with approximately 250,000 cells per well in an appropriate medium for example Dulbecco's Minimal Essential Media (D-MEM) (in the absence of glutamic acid) containing 2 mM glutamine and 10% dialyzed fetal calf serum. After 24 hours growth at 37° C., the media is removed and replaced with fresh media containing four microcuries of [$^3$H] myoinositol per well and the cultures are incubated a further 16 to 20 hours. The media is then removed and the cells in each well are washed with serum free medium containing 10 mM lithium chloride, 10 mM myoinositol, and 10 mM HEPES (2×1 mL washes). After the final wash, 0.5 mL of washing solution is added containing the appropriate concentration(s) of test compound(s).

If the particular assay is also testing antagonists, a ten minutes incubation is performed prior to antagonist induction. Cells are incubated for about one hour at 37° C. in 95%:5% $O_2$: $C_2$ or as appropriate for time course. The reactions are terminated by removing media and adding 1 mL of cooled 1:1 acetone:methanol followed by incubation on ice for a minimum of twenty minutes.

These extracts are then collected and placed in 1.5 mL centrifuge tubes. Each well is washed with 0.5 mL water and this wash is added to the appropriate extract. After mixing and centrifugation, each aqueous supernatant is processed by chromatography on a QMA SEP-PAK® column, which is prewetted and equilibrated by passing 10 mL of water, followed by 8 mL of 1M triethylammonium hydrogen carbonate (TEAB), followed by 10 mL of water through the column.

The assay supernatants containing the water soluble [$^3$H] inositol phosphate are passed over the columns. This is followed by a 10 mL water wash and a 4 mL wash with 0.02 M TEAB to remove [$^3$H]inositol precursors. [$^3$H]inositol phosphate is eluted with 4 mL of 0.1 M TEAB into scintillation vials and counted in the presence of scintillation cocktail. Total protein in each sample is measured using standard techniques. Measurements are taken as the amount of [$^3$H]inositol phosphate released per milligram of protein.

The assays are carried out in the absence and in the presence of the compound being tested. The measurements of [$^3$H]inositol phosphate per milligram of protein are compared in order to confirm agonist and antagonist activity of the compound being tested.

These types of assays, employing cell lines expressing different subtype of cloned metabotropic receptors, may be used to determine which compounds have selective affinity in that they modulate one subtype of receptor with a greater activity than another subtype.

(c) Testing in Chinese hamster cell lines

The Chinese hamster ovary cell lines expressing mGluR$_{1\alpha}$, mGlu R$_2$ and mGluR$_{4\alpha}$ receptors have been described previously (Amarori and Nakanishi, Neuron 8, 757–765, 1992; Tanabe et al., Neuron 8, 169–179, 1992, and J. Neurochem. 63, 2038–2047, 1993). They are maintained at 37° C. in a humidified 5% $CO_2$ incubator in Dubecco's Modified Eagle Medium (DMEM) containing a reduced concentration of(S)-glutamine (2 mM) and are supplemented with 1% proline, penicillin (100 U/mL), streptomycin (100 mg/mL) and 10% dialyzed fetal calf serum (all GIBCO, Paisley). Two days before assay 1.8×10$^6$ cells are evenly distributed into the wells of 24 well plates.

Phosphatidylinositol (PI) hydrolysis can be measured as described previously (Hayashi et al., Nature 366, 687–690, 1992, and J. Neuroscience 14, 3370–3377, 1994). Briefly, the cells are labeled with [$^3$H]inositol (2 $\mu$Ci/mL) 24 h prior to the assay. For agonist assays, the cells are incubated with test compound dissolved in phosphate-buffered saline (PBS)-LiCl for 20 min, and agonist activity is determined from the level of $^3$H-labeled mono-, bis- and tris-inositol phosphates generated, as measured following ion-exchange chromatography, compared with the level generated in the absence of the test compound. For antagonist assays, the cells are preincubated with ligand dissolved in PBS-LiCl for 20 min prior to incubation with test compound and 10 $\mu$M (S)-Glu for 20 min. The antagonist activity is then determined as the inhibitory effect of the (S)-Glu mediated response.

The assay of cyclic AMP formation can be performed as described previously (Hayashi et al., 1992, 1994). Briefly, the cells are incubated for 10 min in PBS containing test coumpound and 10 $\mu$M forskolin and 1 mM 3-isobutyl-1-methylxanthine (IBMX) (both Sigma, St. Louis, Mo., USA).

The agonist activity is then determined as the inhibitory effect on the forskolin-induced cyclic AMP formation. For antagonist assay, the cells are preincubated with ligand dissolved in PBS containing 1 mM IBMX for 20 min prior to a 10 min incubation in PBS containing test compound, 20 $\mu$M(mGlu2) or 50 $\mu$M (mGlu4a) (S)-Glu, 10 $\mu$M forskolin and 1 mM IBMX The antagonist activity is then determined as the potentiating effect on the forskolin-induced cyclic AMP formation.

Some of the compounds of the invention were tested for antagonist activity against Chinese hamster ovary cell lines expressing cloned mGluR$_{1\alpha}$, mGluR$_2$ and mGluR$_{4\alpha}$ at a concentration of 5 mM. Compounds 4a and 4b of the invention effectively blocked the increase in PI hydrolysis by action of 10 mM (L)-glutamic acid at the mGluR$_{1\alpha}$ receptor. The results are presented in FIG. 1.

Ex Vivo Testing

In vivo testing for demonstration of the pharmacological activity of certain compounds on representative mGlu receptor subtypes can be performed using Sprague Dawley rat tissues.

Phosphatidylinositol (PI) hydrolysis can be measured as described below:

Briefly, cross-chopped slices are prepared from neonatal Sprague Dawley rat tissue (age: p7–p14). The slices are pre-labelled with [$^3$H] myoinositol. Following pre-labelling, the slices are incubated with the test drugs and standard (known Group I agonists i.e. ACPD) for a period of 45 minutes. The incubation is terminated by the addition of chloroform/methanol/HCl (100:200:2). The resulting mixture is separated into two phases by the addition of chloroform and distilled water. The aqueous fraction is applied to ion exchange columns, and inositol phosphates are eluted using 800 mM Ammonium Formate/100 mM Formic Acid. The eluent is then analyzed using liquid scintillation counting. The amount of inositol phosphate accumulation is expressed as a percentage of that induced by ACPD.

The assay of cyclic AMP formation can be performed as described previously (Tovey et al., *Clinica Chimica Acta*, 56, 221–234, 1974). The assay can be modelled On the cyclic AMP assay kit available from Amersham, which in turn, is based on the assay created by Tovey et al. Briefly, samples arm prepared from Sprague Dawley rat (225–250 g) cortical slices. Slices are incubated with the drug, and then challenged with forskolin to induce cyclic ANT release. Following termination of the reaction by boiling, the slices are homogenized and centrifuged. Samples of supernatant are then incubated for 2–3 hours with a known quantity of [$^3$H]cAMP and a binding protein. When the incubation is complete, the bound cyclic AMP is separated from the free cyclic AMP by centrifugation with charcoal. The resulting supernatant (containing free cyclic AMP) is then analyzed by liquid scintillation counting. The amount of unbound cyclic AMP can be calculated from a standard curve previously determined with various samples of free cyclic AMP.

In performing such experiments with some of the compounds of the present invention, it has been demonstrated that some compounds of the present invention act as modulators of the cAMP-linked metabotropic glutamate receptors, while showing less activity with phosphatidylinositol-linked metabotropic glutamate receptors and vice versa.

Administration of Compounds of Formula (I)

According to another aspect, the present invention provides a method of modulating one or more mGluR functions in a warm-blooded mammal which comprises administering an effective amount of a compound of Formula I, or a non-toxic metabolically-labile ester or amide thereof or a pharmaceutically acceptable salt thereof.

The compounds of the present invention are preferably formulated prior to administration. Therefore, another aspect of the present invention is a pharmaceutical formulation comprising a compound of Formula I and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material that acts as a vehicle, excipient, or medium for the active ingredient.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also provides pharmaceutical compositions containing compounds as disclosed in the claims in combination with one or more pharmaceutically acceptable, inert or physiologically active, diluents or adjuvants. The compounds of the invention can be freeze-dried and, if desired, combined with other pharmaceutically acceptable excipients to prepare formulations for administration. These compositions may be presented in any form appropriate for the administration route envisaged. The parenteral and the intravenous route are the preferential routes for administration.

Compounds of the general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and, if desired, other active ingredients. The pharmaceutical compositions containing compounds of general Formula I may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any procedure known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate:

granulating and disintegrating agents for example, corn starch, or alginic acid: binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain active materials in admixture with excipients suitable for the manufacture of aqueous suspensions. Such excipients are suspending agents, for example sodium carboxylmethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxy benzoate, one or more colouring agents, one or more flavouring agents or one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compound(s) of the general Formula I may be administered, together or separately, in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compound(s) of general Formula I may be administered, together or separately, parenterally in sterile medium. The drug, depending on the vehicle and concentration used, can either be suspended or dissolved in the vehicle. Advantageously, adjuvants such as local anaesthetics, preservatives and buffering agents can be dissolved in the vehicle.

The dosage to be administered is not subject to defined limits, but it will usually be an effective amount. It will usually be the equivalent, on a molar basis of the pharmacologically active free form produced from a dosage formulation upon the metabolic release of the active free drug to achieve its desired pharmacological and physiological effects. The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.01 to about 30 mg/kg of body weight. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 |

The above ingredients are mixed and filled into hard gelatin capsules in 460 mg quantities.

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 |

The components are blended and compressed to form tablets each weighing 665 mg.

Formulation 3

An aerosol solution is prepared containing the following components:

|  | Weight % |
| --- | --- |
| Active Ingredient | 0.25 |
| Ethanol | 29.75 |
| Propellant 22 (Chlorodifluoromethane) | 70.00 |
| Total | 100 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

|  | Quantity (mg/tablet) |
| --- | --- |
| Active Ingredient | 60 |
| Starch | 45 |
| Microcrystalline cellulose | 35 |
| Polyvinylpyrrolidone | 4 |
| Sodium carboxymethyl starch | 4.5 |
| Magnesium stearate | 0.5 |
| Talc | 1.0 |
| Total | 150 |

The active ingredient, starch, and cellulose are passed through a No. 45 mesh U.S. sieve and mixed thoroughly. The solution of polyvinylpyrrolidone is mixed with the resultant powders that are then passed through a No. 14 mesh U.S. sieve. The granules so produced are dried at 50° C. and passed through a No. 18 mesh U. S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules each containing 80 mg medicament are made as follows:

|  | Quantity (mg/capsule) |
| --- | --- |
| Active Ingredient | 80 |
| Starch | 59 |
| Microcrystalline cellulose | 59 |
| Magnesium stearate | 2 |
| Total | 200 |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

|  | Quantity (mg/suppository) |
| --- | --- |
| Active Ingredient | 225 |
| Saturated fatty acid glycerides | 2000 |
| Total | 2225 |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 mL dose are made as follows:

| | |
|---|---|
| Active Ingredient | 50 mg |
| Sodium carboxylmethyl cellulose | 50 mg |
| Syrup | 1.25 mL |
| Benzoic acid solution | 0.10 mL |
| Flavour | q.v. |
| Color | q.v. |
| Purified water to total | 5 mL |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | Quantity |
|---|---|
| Active Ingredient | 100 mg |
| Mannitol | 100 mg |
| 5 N Sodium hydroxide | 200 mL |
| Purified water to total | 5 mL |

Formulation 9

A topical formulation may be prepared as follows:

| | Quantity |
|---|---|
| Active Ingredient | 1–10 g |
| Emulsifying Wax | 30 g |
| Liquid Paraffin | 20 g |
| White soft paraffin to | 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation 10

Sublingual or buccal tablets, each containing 10 mg of active ingredient, may be prepared as follows:

| | Quantity (mg/tablet) |
|---|---|
| Active Ingredient | 10.0 |
| Glycerol | 210.5 |
| Water | 143.0 |
| Sodium Citrate | 4.5 |
| Polyvinyl Alcohol | 26.5 |
| Polyvinylpyrrolidone | 15.5 |
| Total | 410.0 |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogeneous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts.

The construction and use of transdermal patches for the delivery of pharmaceutical agents is well known in the art (see, for example, U.S. Pat. No. 5,023,252, issued Jun. 11, 1991) herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions that can transiently open the blood-brain barrier.

EXAMPLES

To gain a better understanding of the invention described herein, the following examples are set forth. It should be understood that these examples are for illustrative purposes only. Therefore, they should not limit the scope of this invention in any way.

The following abbreviations are used in the Examples: EtOAc, ethyl acetate; THF, tetrahydrofuran; EtOH, ethanol; TLC, thin layer chromatography; GC, gas chromatography; HPLC, high pressure liquid chromatography; m-CPBA, m-chloroperbenzoic acid; $Et_2O$, diethyl ether; DMSO, dimethyl sulfoxide; DBU, 1,8-diazabicyclo-[5.4.0]undec-7-ene, MTBE, methyl t-butyl ether, and FDMS, field desorption mass spectrometry.

Example 1

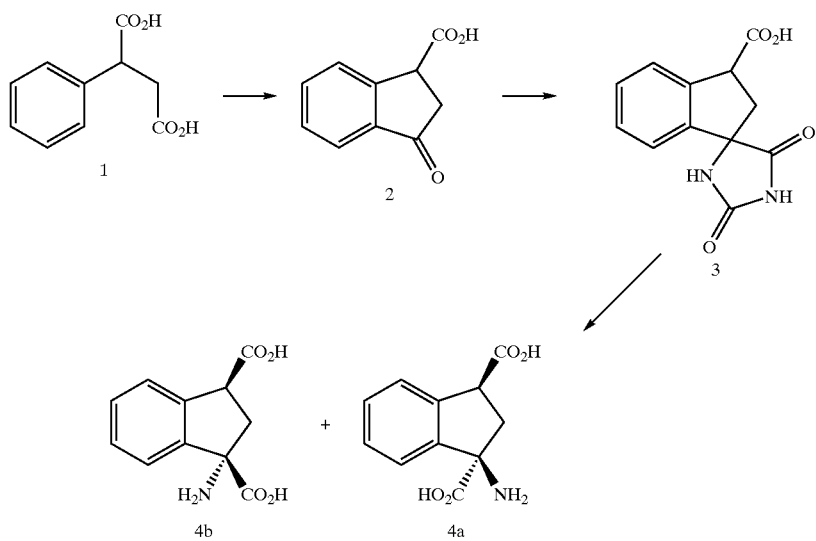

Preparation of 3-Carboxy-1-indanone (Compound 2)

In a 3-neck round bottomed flask, fitted with a gas adapter and a reflux condenser, 4.0 g of phenylsuccinic acid (1) and 4 mL of thionyl chloride were refluxed for 30 min. The reaction mixture was diluted with 8 mL of nitrobenzene and 4 g of aluminum chloride added in one portion. The resulting mixture was stirred at 85° C. for 1.5 h. The resulting mixture was poured into 125 mL of water and the nitrobenzene removed by steam distillation. The product was crystallized and re-crystallized from water to obtain 2.9 g (80%) of compound 2.

$^1$H NMR(CDCl$_3$) δ 2.92 (dd, 1H), 3.15 (dd, 1H), 4.35 (m, 1H) 4.95 (br, 1H), 7.4–7.85 (m, 4H).

Preparation of Cis- and Trans-3-carboxy-1-indane-5,5'-hydantoin (Compound 3)

1.76 g (1.0 mmol) of the keto acid (2) was dissolved in 20 mL of water in a sealed tube together with 0.65 g (1.0 mmol) of potassium cyanide and 1.92 g of ammonium carbonate (2.0 mmol). The solution was stirred and heated to 90–100° C. for 16 h. The resulting dark solution was cooled and acidified with 6 N HCl and concentrated to a residue containing (3) which was extracted into ethanol, filtered and used without further purification.

Preparation of Cis- and Trans-1-aminoindane-1,3-dicarboxylic Acid (4a and 4b)

The residue containing compound (3) above was placed in a round bottomed flask and refluxed together with 45 mL of 2 N NaOH for 16 h. The resulting solution was cooled, acidified with 6 N HCl and extracted into ethanol. The ethanolic solution was treated with propylene oxide to precipitate a mixture of crude (4a and 4b). Chromatography on Spectrum 1×4 anion exchange resin with dilute acetic acid gave the separate isomers as colourless crystals, recrytalized from methanol/water.

$^1$H NMR (D$_2$O) δ 2.30 (dd, 1H), 2.85 (dd, 1 H), 4.05 (m, 1H), 7.2–7.4 (m, 4H) for cis isomer. For trans isomer 2.70 (dd, 1H), 3.10 (dd, 1 H), 4.42 (m, 1H), 7.35–7.55 (m, 4H).

Example 2

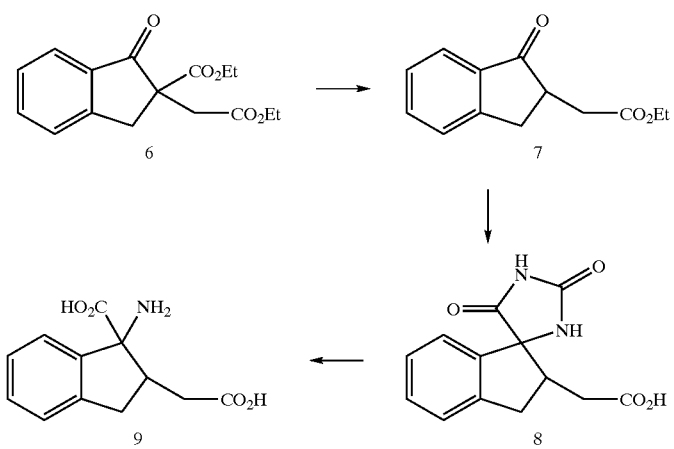

Preparation of 1-Oxoindane-2-acetic Acid (Compound 7)

In a 3-neck flask, fitted with a pressure equalized dropping funnel and a gas inlet adapter, 3.4 g of sodium hydride and 14.2 g of diethyl carbonate in 40 mL of dimethylformarnide (DMF) was stirred at 65° C. A solution of 4 g of 1-indanone (5) in 10 mL DMF was added slowly and the reaction was monitored by TLC (ethyl acetate:hexanes 2:3). On completion of the reaction a solution of 7.5 g of ethylbromoacetate in 20 mL DMF was added and the reaction was stirred at 65° C. for additional 1 h. The reaction mixture was cooled and neutralized with glacial acetic acid. The solution is then evaporated to remove solvents and taken up in 50 mL of diethyl ether. The ethereal solution was washed successively with water and brine, finally dried over magnesium sulphate, filtered and evaporated to yield compound (6) as a gum. Compound (6) was used in the next reaction without further purification. Compound (2) was suspended in 25 mL of 1:1 6 N HCl:acetic acid and refluxed for 3 h. The resulting solution was diluted with 50 mL of water and extracted with ethyl acetate (3×20 mL). The organic layers were combined and dried over magnesium sulphate, filtered and evaporated to give compound (7) as a gum. Flash chromatography on silica (ethyl acetate:hexanes 1:1) gave pure compound (3) as a pale yellow solid. $^1$H NMR (CDCl$_3$) δ 2.60 (dd, 1H), 2.80–3.15 (m, 3H), 3.42 (dd, 1H).

Preparation of 1-Indane-2-acetic Acid-5,5'-hydantoin (Compound 8)

1.76 g (1.0 mmol) of the keto acid (7) was dissolved in 20 mL of water in a sealed tube together with 0.65 g (1.0 mmol) of potassium cyanide and 1.92 g of ammonium carbonate (2.0 mmol). The solution was stirred and heated to 90–100° C. for 16 h. The resulting dark solution was cooled and acidified with 6 N HCl and concentrated to a residue of compound (8), that was extracted into ethanol, filtered and used without further purification.

Preparation of 1-Amino-1-carboxyindane-2-acetic Acid (Compound 9)

The residue containing compound (8) as formed above was placed in a round bottomed flask and refluxed in 45 mL of 2 N NaOH for 16 h. The resulting solution was cooled, acidified with 6 N HCl, evaporated to dryness and extracted into ethanol. The ethanolic solution was treated with propylene oxide to precipitate a mixture of crude compound (9). Chromatography on Spectrum 1×4 anion exchange resin, with dilute acetic acid gave compound (9) as colourless crystals from methanol/water. $^1$H NMR (D$_2$O) 2.58 (dd, 1H), 2.80–3.05 (3H), 3.42 (dd, 1H), 7.30–7.50 (2H), 7.58 (m, 1H), 7.75 (d, 1H).

Example 3

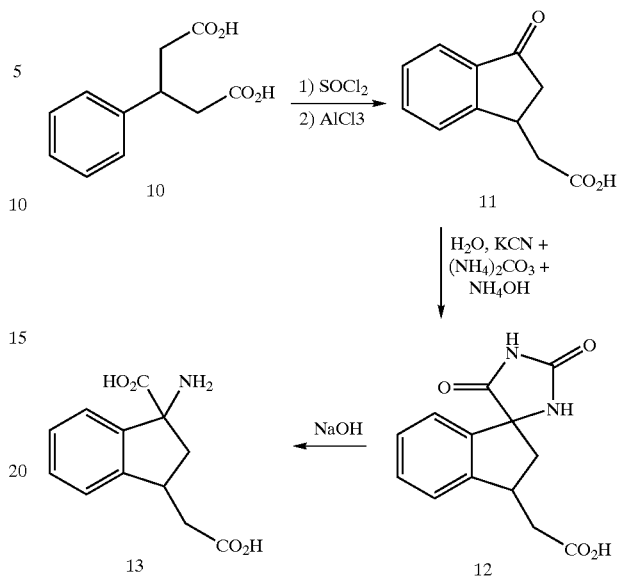

Preparation of Indan-2-one-1-acetic Acid (Compound 11)

A mixture of phenylglutaric acid (4.8 g, 0.023 mol) and thionyl chloride (4.8 mL) in a round-bottom flask was heated to reflux for 30 minutes, followed by addition of 10 mL of nitrobenzene and aluminium chloride (4.8 g) to the mixture, respectively. The resulting mixture was heated to 80° C. for 1.5 h. The mixture was pored into water (120 mL) and nitrobenzene was removed by steam distillation. The residue was washed with water to yield 3.9 g (90%) of compound 11 as a pale solid.

Preparation of 1-Amino-1-carboxyindane-3-acetic Acid (13)

In a sealed pressure glass bottle, heated a mixture of compound 11 (1.90 g, 0.010 mol), KCN (1.61 g, 0.025mol), (NH4)$_2$CO$_3$ (6.69 g 0.070 mol) and NH$_4$OH (1 mL) in 40 mL of water/ethanol (1:1), at 90–100° C. for 16 hours. The mixture was allowed to cool, acidified with 6N HCl, and concentrated in vacuo. The residue was taken up in EtOH and filtered and the filtrate was concentrated in vacuo. 45 mL of 2N NaOH was added to the residue and t the mixture was heated to reflux for 16 hours. The mixture was allowed to cool and acidified with 6N HCl and the resulting mixture was concentrated in vacuo. The residue was taken up in EtOH and filtered. Propylene oxide (10 mL) was added to the filtrate and resulting precipitates were filtered to obtain 1.41 g (77%) of compound 13 as solid.

Example 4

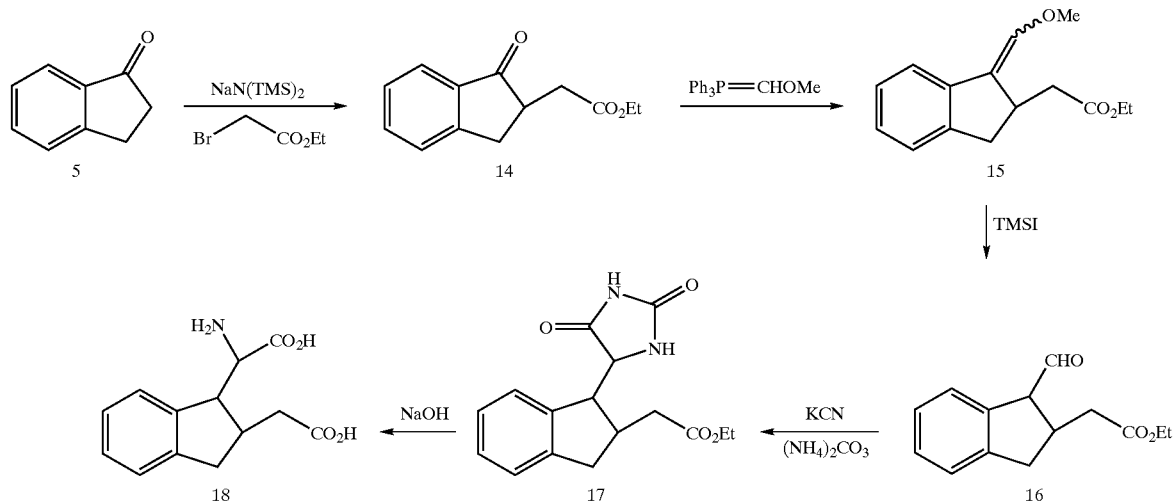

Preparation of Intermediate Compound (14)

Sodium bis(trimethylsilyl)amide (39.0 mL) was added to a stirred solution of 1-indanone (5 g) in dry THF (123 mL) at −75° C. under $N_2$ over 20 minutes. To the mixture was added a solution of ethylbromoacetate (4.41 mL) in dry THF (30 mL) over 25 minutes and maintained at −75° C. for 35 minutes. (The solution turns cloudy after 10 minutes). The mixture was warmed to −10° C. over 3 hours and 30 mL of $H_2O$ added and the pH adjusted to about 7. The solvent was removed by rotary evaporation and the residue diluted with brine (200 mL). The suspension was extracted with EtOAc (4×200 mL. The EtOAc solution was dried over $MgSO_4$ and concentrated to yield an oil (~9 g). The product was purified by column chromatography (hexanes:acetone, 9:1). Yield 4.31 g (52.2%).

Preparation of Intermediate Compound (15)

Sodium bis(trimethylsilyl)amide (26.7 mL) was added to a stirred suspension of (methoxy methyl) triphenylphosphonium chloride (9.5024 g) in dry THF (80 mL) at 0° C. under $N_2$. The resulting red mixture was stirred at 0° C. for 35 minutes and a solution of 13 (4.31 g) in dry THF (40 mL) added over 10 minutes. The mixture was stirred at 0° C. for 2 hours and at room temperature for 1 hour. Water (30 mL) was added and the mixture waspartitioned between brine (200 mL) and EtOAc (200 1L). The organic phase was washed with brine (2×150 mL) concentrated. The crude product was purified by column chromatography (hexanes:EtOAc, 9:1). To obtain 3.11 g (64%) of compound 15.

Preparation of Intermediate Compound (16)

To a stirred solution of 15 and pyridine (0.429 mL) in $CHCl_3$ (292 mL) was added trimethylsilyl iodide (3.2 mL) at 0° C., under $N_2$ over 7 minutes. The resulting cloudy mixture was stirred at 0° C. for 1.5 hours, and a further aliquot of TMSI (0.3 11L) aws added. After 40 min 80 mL of ice-cold 5% $NaHCO_3$ solution was added and the mixture stirred at 0° C. for 10 minutes and partitioned between brine (500 mL) and EtOAc (800 mL). The aqueous phase was extracted with EtOAc (2×200 mL) and the combined EtOAc extracts were washed with brine (2×200 mL). The EtOAc extracts were dried over $MgSO_4$ and evaporated. The crude product was purified by column chromatography (hexanes: EtOAc, 8:1→85:15) to obtain 1.89 g (63.9%) of compound 16.

Preparation of Compound (18)

A solution of compound 16 (1.89 g), KCN (1.332 g), and $(NH_4)_2CO_3$ (5.4974 g) in EtOH (20 mL) and $H_2O$ (20 mL) was heated in a sealed pressure tube at 85–90° C. for 18 hours. 0.65 g of KCN and 2.75 g of $(NH_4)_2CO_3$ was added and the reaction mixture was stirred for 2 days. The reaction mixture was cooled and acidified with 6N HCl to pH 2 and the solvents were removed by rotary evaporation. The residue was extracted into EtOH and filtered, and 277 mg (13.8% from 16) of amino acid 18 was isolated by addition of propylene oxide. Anal. Calculated for compound 18: C; 62.64, H; 6.07, N; 5.62. Found: C; 61.89, H; 6.18, N; 5.51, contains 0.2 mol $H_2O$ $^1$H NMR ($D_2O$) δ 2–2.8 (m, 3H), 3.05–3.2 (m 2H), 3.5–3.7 (dd 1H), 4.2 (d 1H), 7.25 (s 4H).

Example 5

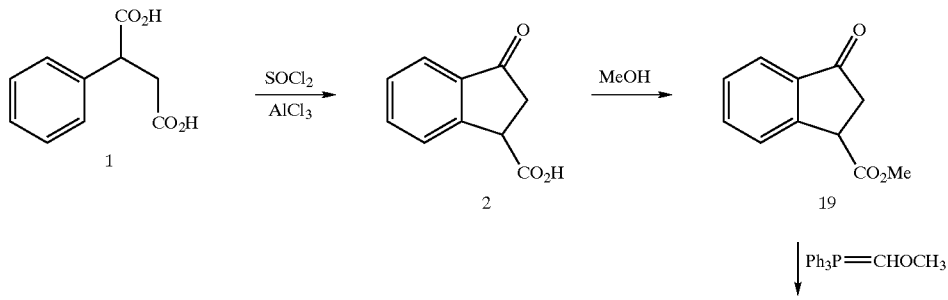

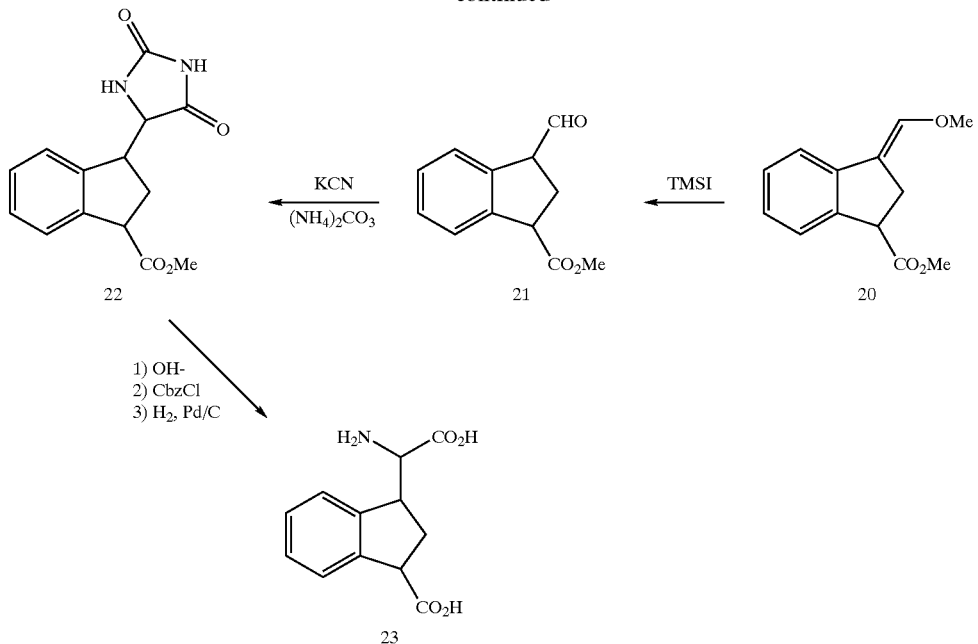

Preparation of Intermediate Compound (2)

A suspension of compound 1 (4 g) in SOCl$_2$ (5 mL) was refluxed with stirring for 35 minutes. Nitrobenzene (20 mL) and anhydrous AlCl$_3$ (4 g) were added and the mixture stirred at 80° C. for 1 hour and 45 minutes, the mixture was poured into water (125 mL) and most of the solvent removed by rotary evaporation. The residue was suspend in water (300 mL), extracted with EtOAc (3×200 mL). The combined EtOAc extracts were washed with brine, dried and concentrated. The product was purified by column chromatography (hexanes:EtOAc:HCO$_2$H, 6:4:0.1) to obtain 2.91 g of compound 2 as pale brown solid.

Preparation of Intermediate Compound (19)

DCC (1.47 g) was added to a stirred solution of compound 2 (1.045 g) in MeOH (dry, 1.3 equivalents) and dry CH$_2$Cl$_2$ (50 mL), followed by 5 mg of DMAP. The mixture was stirred overnight and the resulting suspension filtered through paper. The solvent was removed by rotary evaporation and the residue was purified by column chromatography (hexanes:EtOAc, 75:25) to obtain 0.849 g of compound 19 as pale brown solid.

Preparation of Intermediate Compound (20)

1 M of NaN$_3$(TMS)$_2$ (31.73 mL) in THF was added to a stirred suspension of Ph$_3$PCH$_2$OCH$_3$Cl (11.25 g) in dry THF (90 mL) at 0° C. under N$_2$. After 55 minutes a solution of compound 19 (4.2864 g) in THF was added over 25 minutes. The mixture was stirred at 0° C. for 2 hours and at room temperature overnight. The mixture was diluted with 500 mL of water and extracted with EtOAc (4×150 mL), the organic extracts were washed with brine, dried and concentrated. The crude product was purified by column chromatography (hexanes: EtOAc, 9:1) to obtain 1.617 g of compound 20 as a clear oil.

Preparation of Intermediate Compound (21)

TMSI (1.56 mL) was added to a stirred solution of compound 20 (1.4367 g) and pyridine (0.21 mL) in dry CHCl$_3$ (140 mL) under N$_2$ at 0° C. the mixture was stirred at 0° C. for 1.5 hours and more TMSI (0.8 mL) was added. After stirring at 0° C. for 0.5 hours, and then at room temperature for 2 h, the mixture was cooled again to 0° C. and 5% NaHCO$_3$ added to quench the reaction. The resulting mixture was diluted with EtOAc, washed with brine once, diluted Na$_2$S$_2$O$_3$ solution, brine (twice), dried and concentrated. The product was purified with column chromatography (hexanes:EtOAc, 8:2) to obtain 0.68 g of compound 21 as a faint yellow oil.

Preparation of Intermediate Compound (23)

A mixture of compound 21 (0.65 g), KCN (0.54 g) and (NH$_4$)$_2$CO$_3$ (2.2319 g) in a solution of EtOH/H$_2$O (8 mL/8 mL) was stirred in a pressure tube at −100° C. for 3 days. More KCN (0.27 g) and (NH$_4$)$_2$CO$_3$ (1.11 g) were added to the mixture after 27 hours. The mixture was cooled down to room temperate and acidified with 6 N HCl to pH~2, and the solvents removed by rotary evaporation. MeOH was added to the residue and the resulting suspension was filtered. The filtrate was concentrated and the resulting residue was dissolved in 3 N NaOH (40 mL) and refluxed for 2 days. The obtained crude product was re-dissolved in 2 N NaOH/1,4-dioxane (13mL:13 mL) and CbzCl (0.67 mL) was added at 0° C., while stirring. The mixture was stirred for 1 hour at 0° C. and at room temperature for 2 days. More CbzCl was added to the reaction mixture (0.9 mL after 7 hours, 0.5 mL after 1 day) and 2 N NaOH added to adjust the pH to ~9.

The mixture a extracted with EtOAc (4×150 mL). The aqueous solution was cooled to 0° C., acidified with 6 N HCl to pH ~2 and extracted with EtOAc (4×150 mL). Combined organic extracts were washed with brine (2×100 mL), dried and concentrated. The crude product was purified by column chromatography (CH$_2$Cl$_2$: Acetone: HCO$_2$H, 85:15:1) to obtain protected form of compound 23. This product was hydrogenized in 20 mL MEOH with 10% Pd/C (18 mg) under H$_2$ for 24 hours. The solution was filtered through Celite and crystallized from MeOH to obtain 82.4 mg of compound 23 as an off-white solid. Elemental analysis calc.

for compound 23: C; 60.12, H; 5.68, N.; 5.84. Found: C; 60.11, H; 5.55, N; 5.79. $^1$H NMR (D$_2$O) δ 2.2 (t, 2H), 3.6–3.8 (m, 2H due to overlapping single protons), 3.9 (d, 1H), 7.3 (s, 4H).

Example 6

Ex Vivo Testing of Exemplary Compounds

Cyclic AMP assay:

Rationale:

Group II/III metabotropic glutamate receptors (mGluRs) are negatively coupled to adenylate cyclase, and agonists of these receptors lead to a decrease in intracellular cyclic AMP accumulation.

Method:

The assay has been modeled on the cyclic AMP assay kit available from Amersham. This kit in turn, is based on the assay created by Tovey et al. (1974). Briefly, the samples were prepared from Sprague Dawley rat (225–250 g) cortical slices. Slices were incubated with the test compound (drug), and then challenged with forskolin to induce cyclic AMP release. Following termination of the reaction by boiling, the slices were homogenized and centrifuged. Samples of supernatant were then incubated for 2–3 hours with a known quantity of [$^3$H]cAMP and a binding protein. When the incubation was complete, the bound cyclic AMP was separated from the free cyclic AMP by centrifugation with charcoal. The resulting supernatant (containing free cyclic AMP) was then analyzed by liquid scintillation counting. The amount of unbound cyclic AMP was calculated from a standard curve previously determined with various samples of free cyclic AMP.

Results Interpretation:

If the drugs tested inhibit forskolin-induced cyclic AMP accumulation, they are considered to be Group II/III agonists. Conversely, if they inhibit the decrease in forskolin-induced cyclic AMP accumulation caused by glutamate, they are considered to be Group II/II antagonists.

Results:

| Aminoindane | Group II/III Agonist | EC$_{50}$ (M) | Group II/III Antagonist | EC$_{50}$ (M) |
|---|---|---|---|---|
| Trans-1-aminoaindane-1,3-dicarboxylic acid Compound 4a | No | — | No | — |
| Cis-1-aminoindane-1,3-dicarboxylic acid Compound 4b | Yes | 2.1 × 10$^{-6}$ | No | — |
| Trans-1-amino-1-carboxyindane-2-acetic acid Compound 9 | No | — | Yes | 3.4 × 10$^{-8}$ |
| Trans-1-amino-1-carboxyindane-3-acetic acid Compound 13 | Yes | 9.9 × 10$^{-7}$ | No | — |
| 1-[2-amino]-2-indanediacetic acid Compound 18 | Yes | 4.6 × 10$^{-7}$ | Yes | 2.6 × 10$^{-8}$ |
| 1-[2-amino]-3-carboxyindaneacetic acid Compound 23 | No | — | Yes | 6.1 × 10$^{-7}$ |

Phosphatidylinositol Assay

Rationale:

Group I metabotropic glutamate receptors (mGluRs) are positively coupled on inositol phosphate metabolism. Agonists at these receptors lead to an increase in intracellular free inositol phosphates, while antagonists inhibit the increase in intracellular free inositol phosphate induced by standard agonists (i.e. ACPD).

Method:

Cross-chopped slices were prepared from neonatal Sprague Dawley rat tissue (age: p7–p14). The slices were pre-labelled with [3H] myo-inositol. Following pre-labelling, the slices were incubated with the test compounds and standard (known Group I agonists i.e. ACPD) for a period of 45 minutes. The incubation was terminated by the addition of chloroform/methanol/HCl (100:200:2). The resulting mixture was separated into two phases by the addition of chloroform and distilled water. The aqueous fraction was applied to ion exchange columns, and inositol phosphates were eluted using 800 mM Ammonium Formate/100 mM Formic Acid. The eluent was then analyzed using liquid scintillation counting. The amount of inositol phosphate accumulation was expressed as a percentage of that induced by ACPD.

Results Interpretation:

If the drugs cause an increase in intracellular free inositol phosphate accumulation, they are considered to be Group I agonists. If they inhibit the increase in intracellular free inositol phosphate accumulation induced by ACPD, they are considered to be Group II antagonists.

Results:

| Aminoindane | Group I Agonist | EC$_{50}$ (M) | Group I Antagonist | EC$_{50}$ (M) |
|---|---|---|---|---|
| Trans-1-aminoaindane-1,3-dicarboxylic acid Compound 4a | No | — | Yes | 4.8 × 10$^{-7}$ |
| Cis-1-aminoindane-1,3-dicarboxylic acid Compound 4b | No | — | No | — |
| Trans-1-amino-1-carboxyindane-2-acetic acid Compound 9 | No | — | Yes | 1.1 × 10$^{-6}$ |
| Trans-1-amino-1-carboxyindane-3-acetic acid Compound 13 | No | — | Yes | 1.3 × 10$^{-9}$ |
| 1-[2-amino]-2-indanediacetic acid Compound 18 | No | — | Yes | 1.4 × 10$^{-5}$ |
| 1-[2-amino]-3-carboxyindaneacetic acid Compound 23 | No | — | No | — |

The invention being thus described, it will be obvious that the same may be varied in many ways. Those skilled in the art will recognize that other and further changes and modifications may be made thereto without departing from the spirit of the invention, and it is intended to claim all such changes and modifications as fall within the scope of the invention.

What is claimed is:

1. A compound having structural formula (I):

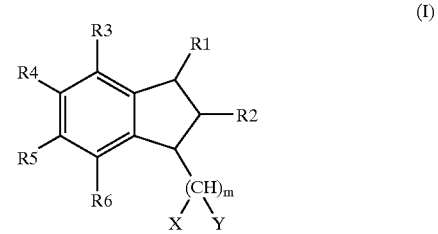

or stereoisomers, pharmaceutically acceptable salts, or hydrates thereof, wherein:

R1 and R2 are independently:

H, or an acidic group selected from the group consisting of carboxy and —(CH$_2$)$_n$-carboxy, where n=1, 2, 3, 4, 5, or 6;
X is an acidic carboxy group;
Y is a basic group selected from the group consisting of aliphatic 1° amino, aliphatic 2° amino, aliphatic 3° amino, aliphatic quaternary ammonium salts, aromatic 1° amino, aromatic 2° amino, aromatic 3° amino, and aromatic quaternary ammonium salts;
m is 0 or 1; and
R3, R4, R5, and R6 are independently selected from the group consisting of H, nitro, amino, halogen, trifluoromethyl, trifluoroacetyl, sulfo, carboxy, carbamoyl, and sulfamoyl, or pharmaceutically acceptable salt thereof;
with the proviso that
at least one of R1 and R2 is carboxy or —$(CH_2)_n$-carboxy.

2. The compound according to claim 1, wherein said compound is selected from the group consisting of:

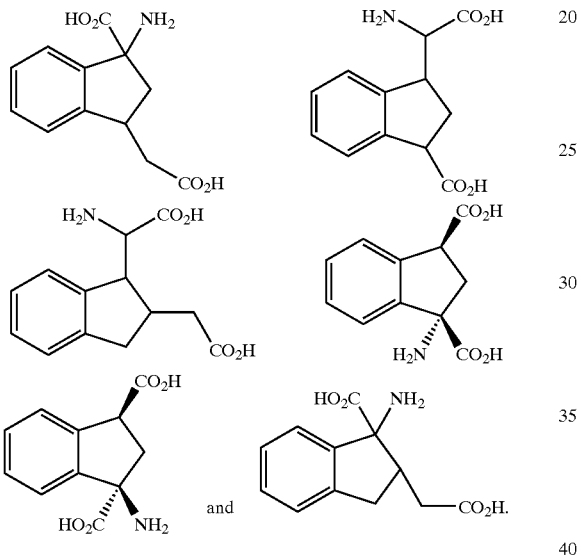

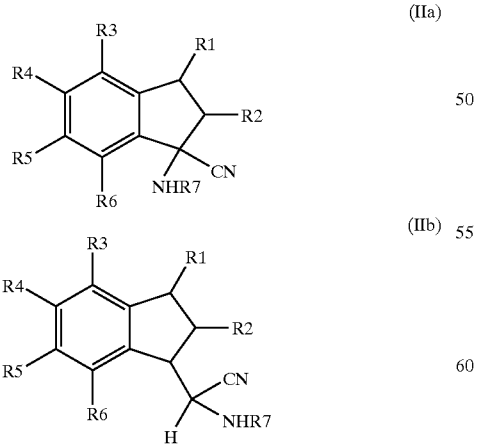

3. A process for the preparation of a compound of Formula I, according to claim 1, or a pharmaceutically acceptable salt thereof, which comprises:

a) hydrolyzing a compound of formula (IIa) or (IIb):

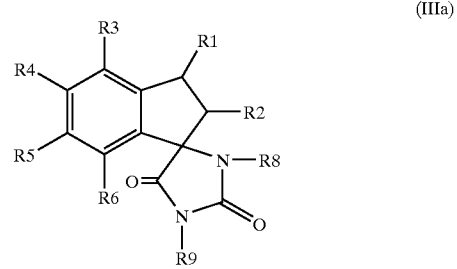

(IIa)

(IIb)

wherein R1 and R2 are independently:
H, or an acidic group selected from the group consisting of carboxy and —$(CH_2)_n$-carboxy, wherein n=1, 2, 3, 4, 5, or 6; and
R3, R4, R5 and R6 are independently selected from the group consisting of H, nitro, amino, halogen, trifluoromethyl, trifluoroacetyl, sulfo, carboxy, carbamoyl, and sulfamoyl, or a pharmaceutically acceptable salt thereof, and wherein R7 is a hydrogen atom or an acyl group; or b) hydrolyzing a compound of formula (IIIa) or (IIb):
wherein R1, R2, R3, R4, R5 and R6 are as defined above, R8 and R9 each

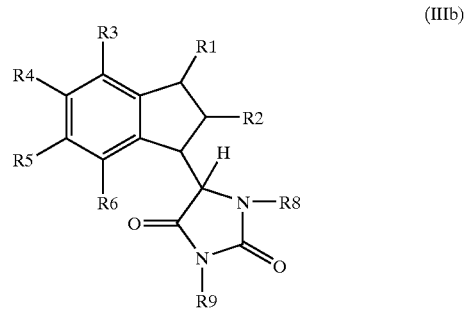

(IIIa)

(IIIb)

independently represent a hydrogen atom, a ($C_2$–$C_6$) alkanoyl group, a ($C_{1-4}$) alkyl group, a ($C_3$–$C_4$) alkenyl group or a phenyl ($C_{1-4}$) alkyl group wherein the phenyl is unsubstituted or substituted with halogen, ($C_{1-4}$) alkyl or ($C_1$–$C_4$) alkoxy, or a salt thereof; or c) deprotecting a compound of formula (IVa) or (IVb):

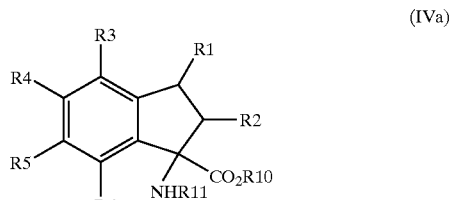

(IVa)

(IVb)

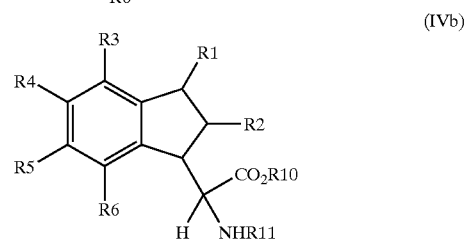

wherein R1, R2, R3, R4, R5 and R6 are as defined above and R10 is a hydrogen atom or a carboxyl protecting group, or a salt thereof, and R11 represents a hydrogen atom or a nitrogen protecting group; and
whereafter, if necessary and/or desired, the following steps are carried out:

(i) resolving the compound of Formula I;
(ii) converting the compound of Formula I into a non-toxic metabolically labile ester or amide thereof and/or;
(iii) converting the compound of Formula I or a non-toxic metabolically labile ester or amide thereof into a pharmaceutically acceptable salt thereof.

4. A pharmaceutical composition comprising a compound, wherein said compound has the formula:

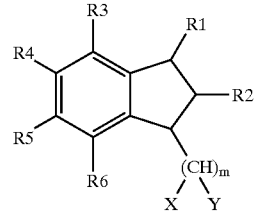
(I)

or said compound is a stereoisomer, or pharmaceutically acceptable salt or hydrate thereof, and a pharmaceutically acceptable carrier, diluent or excipient, wherein:

R1 and R2 are independently selected from the group consisting of:
H, an acidic group selected from the group consisting of carboxy and —$(CH_2)_n$-carboxy,
where n=1, 2, 3, 4, 5, or 6;
X is an acidic carboxy group;
Y is a basic group selected from the group consisting of aliphatic 1° amino, aliphatic 2° amino, aliphatic 3° amino, aliphatic quaternary ammonium salts, aromatic 1° amino, aromatic 2° amino, aromatic 3° amino, and aromatic quaternary ammonium salts;
m is 0 or 1; and
R3, R4, R5, and R6 are independently selected from the group consisting of H, nitro, amino, halogen, trifluoromethyl, trifluoroacetyl, sulfo, carboxy, carbamoyl, and sulfamoyl, or a pharmaceutically acceptable salt thereof;

with the proviso that at least one of R1 and R2 is carboxy or —$(CH_2)_n$ carboxy.

5. The pharmaceutical composition of claim 4, wherein said compound is selected from the group consisting of:

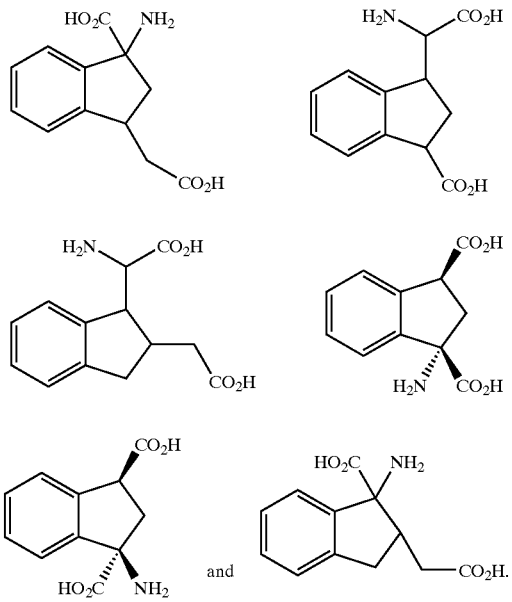

6. The process according to claim 3, wherein R7 is hydrogen or ($C_2$–$C_6$) alkanoyl group.

* * * * *